United States Patent
Tsukagoshi

(10) Patent No.: US 9,814,434 B2
(45) Date of Patent: Nov. 14, 2017

(54) MEDICAL IMAGE DISPLAY APPARATUS AND X-RAY COMPUTED TOMOGRAPHY APPARATUS

(75) Inventor: Shinsuke Tsukagoshi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/161,870

(22) Filed: Jun. 16, 2011

(65) Prior Publication Data
US 2011/0311021 A1   Dec. 22, 2011

(30) Foreign Application Priority Data
Jun. 16, 2010  (JP) .................. 2010-137733

(51) Int. Cl.
 A61B 6/03  (2006.01)
 H04N 7/01  (2006.01)
 A61B 6/00  (2006.01)
 G06F 19/00  (2011.01)

(52) U.S. Cl.
 CPC .............. *A61B 6/469* (2013.01); *A61B 6/461* (2013.01); *A61B 6/481* (2013.01); *A61B 6/486* (2013.01); *G06F 19/321* (2013.01)

(58) Field of Classification Search
 CPC ......... G06T 7/0016; G06T 2207/10124; A61B 6/469; A61B 6/461; A61B 6/486; A61B 6/481; G06F 19/321
 See application file for complete search history.

(56) References Cited

U.S. PATENT DOCUMENTS

| | | | | |
|---|---|---|---|---|
| 5,592,523 A * | 1/1997 | Tuy et al. | ....................... | 378/19 |
| 5,710,572 A * | 1/1998 | Nihei | ............................. | 715/272 |
| 6,426,991 B1 * | 7/2002 | Mattson et al. | ................ | 378/19 |
| 7,403,589 B1 * | 7/2008 | Short et al. | ...................... | 378/19 |
| 2002/0131628 A1 * | 9/2002 | Toda | ..................... | G06F 19/321 382/132 |
| 2006/0013462 A1 * | 1/2006 | Sadikali | ........................ | 382/132 |
| 2006/0050842 A1 * | 3/2006 | Wang | .................. | G01N 23/046 378/16 |
| 2007/0019779 A1 * | 1/2007 | Nishide et al. | .................... | 378/4 |
| 2007/0091204 A1 * | 4/2007 | Koshimizu et al. | .......... | 348/441 |
| 2008/0024599 A1 * | 1/2008 | Hirakawa | ........................ | 348/65 |
| 2009/0010519 A1 * | 1/2009 | Wakai et al. | ................. | 382/131 |
| 2010/0060754 A1 * | 3/2010 | Ogura et al. | .................. | 348/241 |

FOREIGN PATENT DOCUMENTS

| | | |
|---|---|---|
| JP | 7-289546 | 11/1995 |
| JP | 2001-120547 | 5/2001 |
| JP | 2001-242253 A | 9/2001 |
| JP | 2005-277733 A | 10/2005 |
| JP | 2006-149684 A | 6/2006 |
| JP | 2009-142388 A | 7/2009 |

* cited by examiner

*Primary Examiner* — Dani Fox
(74) *Attorney, Agent, or Firm* — Oblon, McClelland, Maier & Neustadt, L.L.P.

(57) ABSTRACT

According to one embodiment, a medical image display apparatus includes a thin-out processing unit configured to execute thin-out processing for a series of original medical images, a display unit configured to display the series of medical images generated by the thin-out processing as a moving image and a control unit. The control unit controls the thin-out processing unit to change thin-out ratios on a time axis in the thin-out processing.

30 Claims, 11 Drawing Sheets

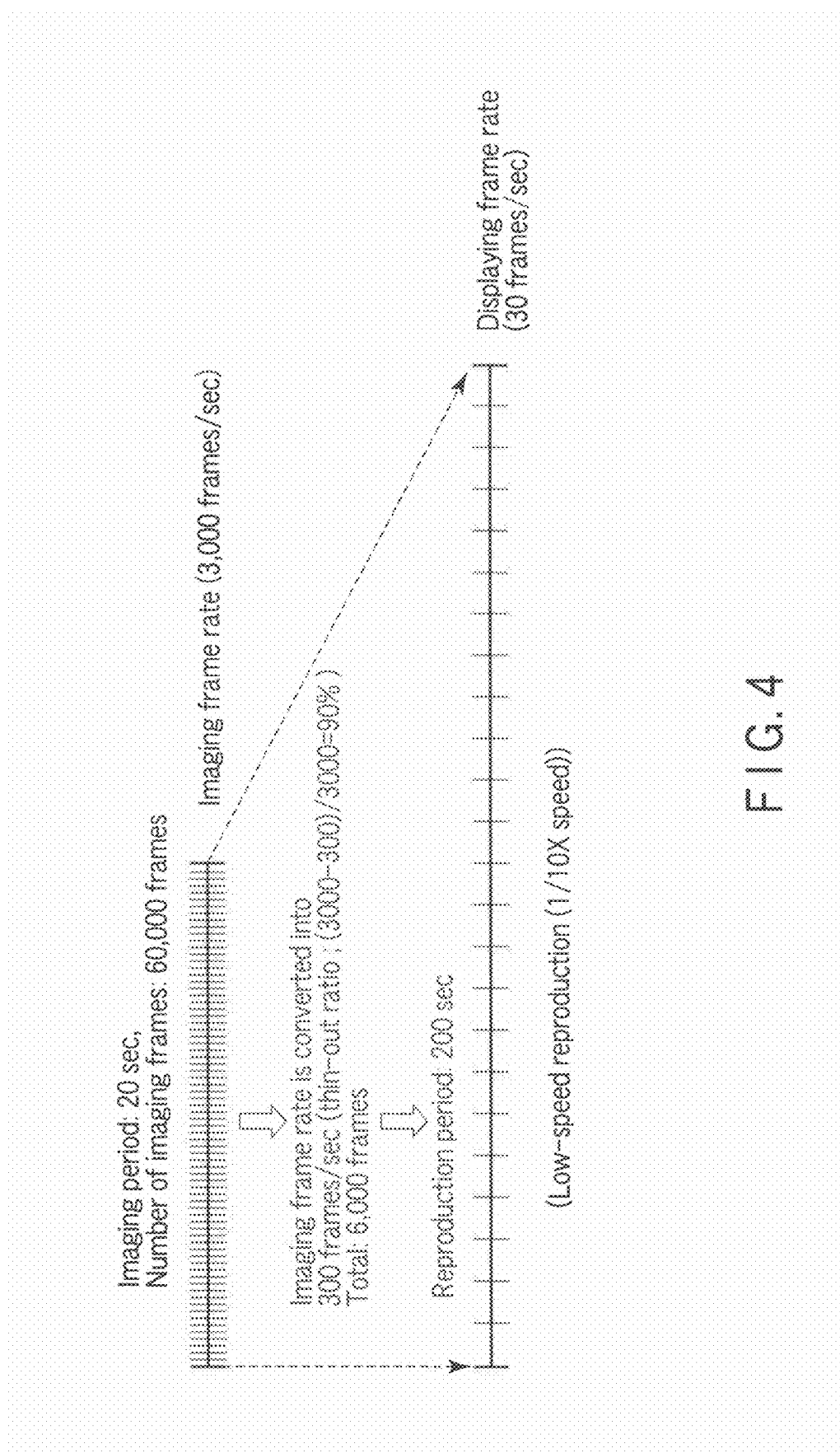
F I G. 4

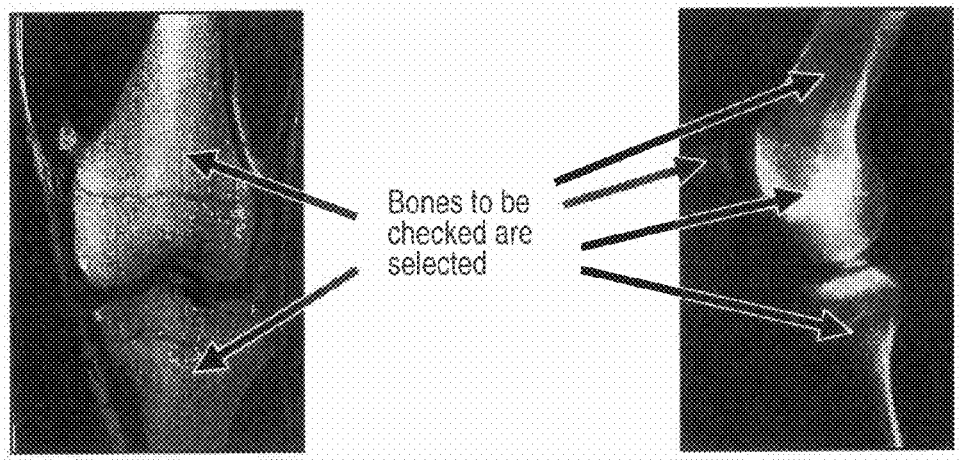
F I G. 18
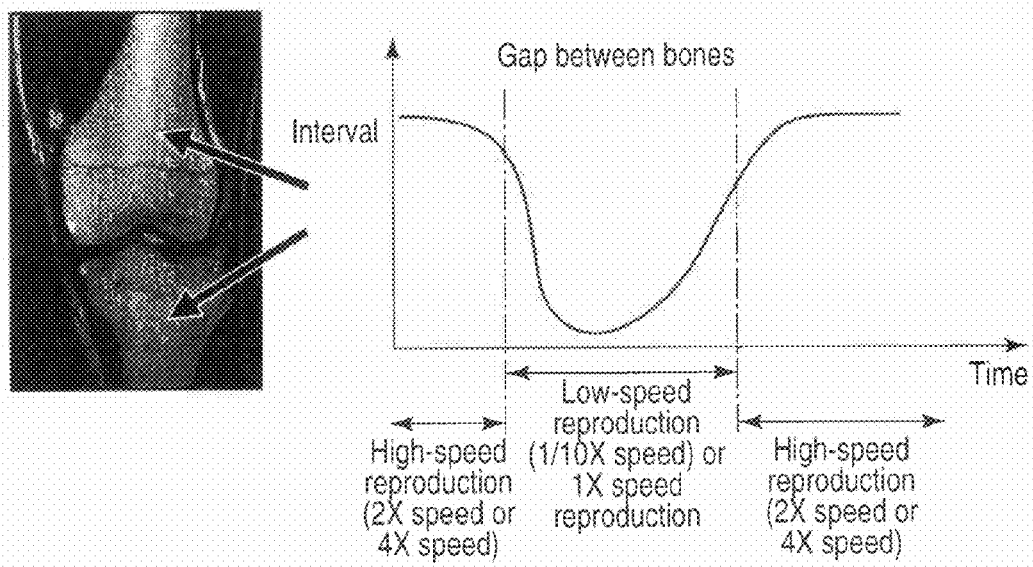
F I G. 19

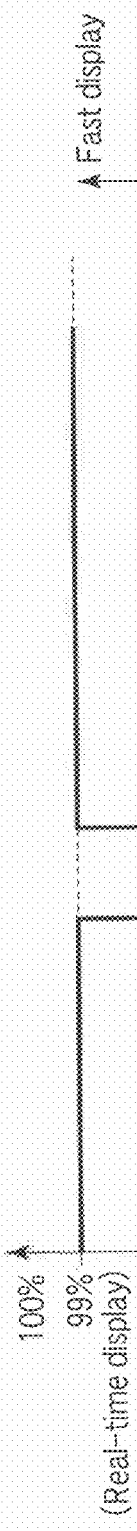
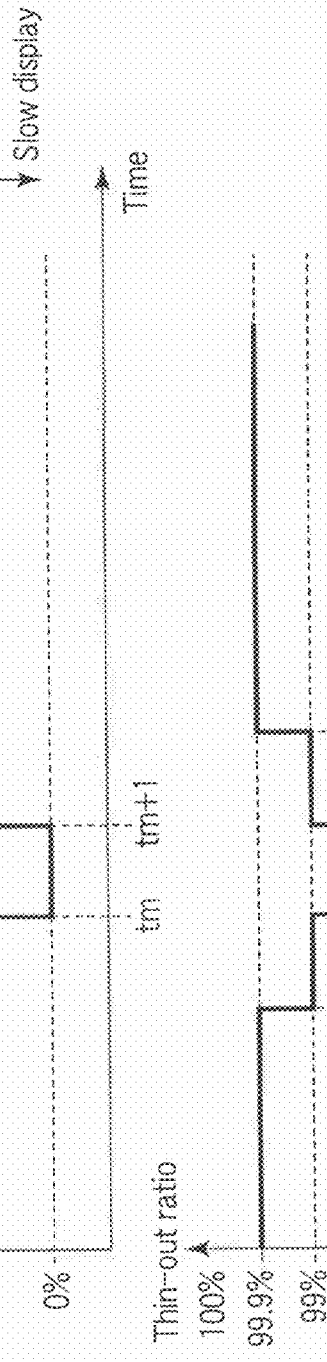
FIG. 20
FIG. 21

MEDICAL IMAGE DISPLAY APPARATUS AND X-RAY COMPUTED TOMOGRAPHY APPARATUS

CROSS-REFERENCE TO RELATED APPLICATIONS

This application is based upon and claims the benefit of priority from Japanese Patent Application No. 2010-137733, filed Jun. 16, 2010; the entire contents of which are incorporated herein by reference.

FIELD

Embodiments described herein relate generally to a medical image display apparatus and an X-ray computed tomography apparatus.

BACKGROUND

The present invention relates to a medical image display apparatus for a large quantity of medical images, as display targets, which are acquired by ultrafast imaging at a frame rate of 3,000 frames/sec, and an X-ray computed tomography apparatus.

Medical imaging, e.g., dynamic imaging for checking the inflow/outflow dynamics of a contrast medium in contrast-enhanced examination, requires about 30 sec to 180 sec. To check the motion of a joint, imaging needs to be executed for about 5 sec to 10 sec. Even, for example, an imaging time of 20 sec will generate medical images as many as 60,000 frames in ultrafast imaging at, for example, 3,000 frames/sec.

As is well known, the maximum frame rate that the human eye can perceive is about 30 frames/sec. It required as long a time as 30 or more min to display medical image as many as 60,000 frames acquired by ultrafast imaging at this displaying frame rate (30 frames/sec).

BRIEF DESCRIPTION OF THE DRAWINGS

FIG. 4 is a view showing low-speed reproduction (1/10× speed) in this embodiment;

FIG. 18 is a view showing the concept of another rule for deciding periods of interest in this embodiment;

FIG. 19 is a view showing the periods of interest decided by the rule in FIG. 18;

FIG. 20 is a graph showing an example of a temporal change in thin-out ratio in this embodiment; and FIG. 21 is a graph showing another example of a temporal change in thin-out ratio in this embodiment.

DETAILED DESCRIPTION

Figure 1:
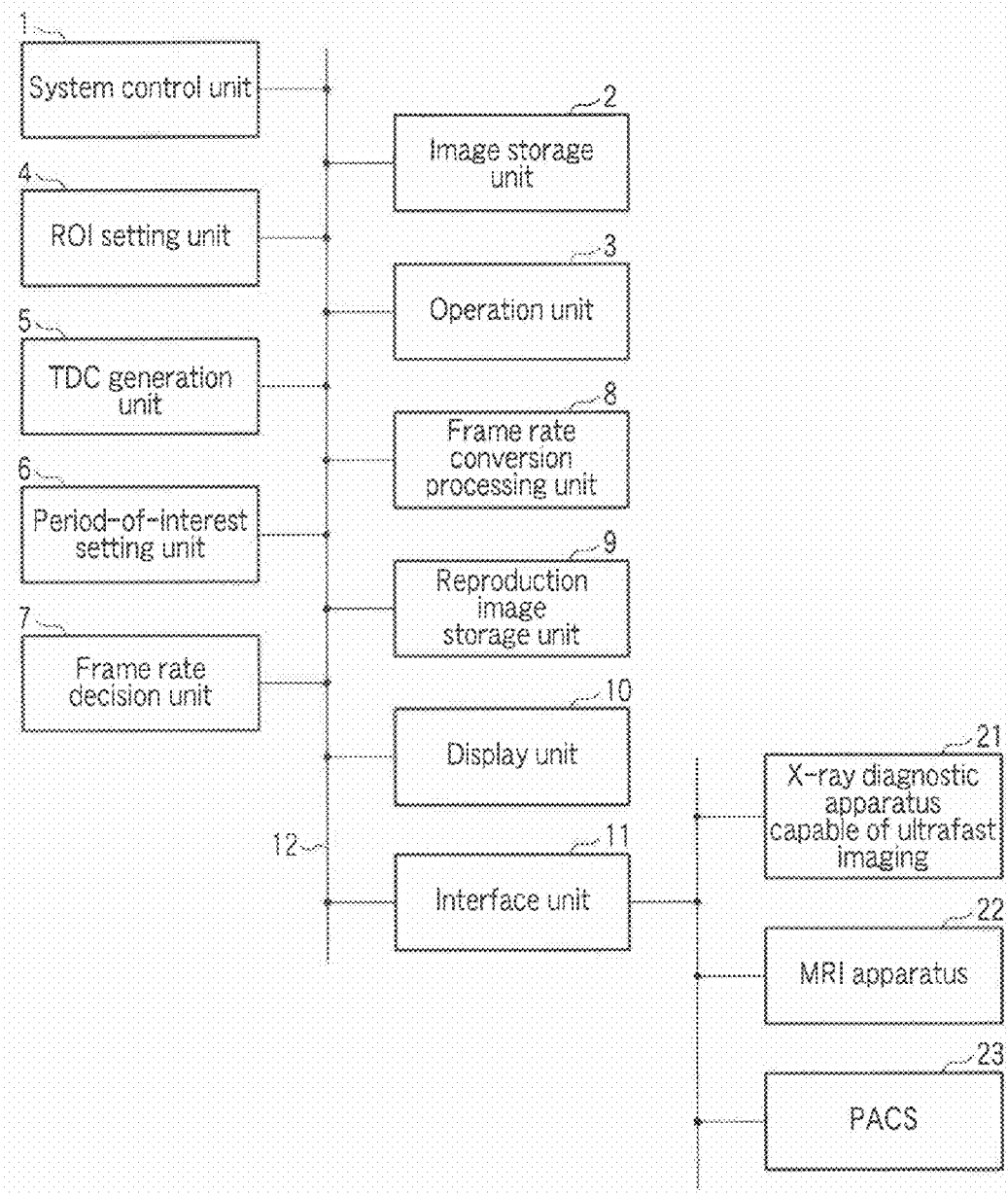
FIG. 1 is a block diagram showing the arrangement of an image display apparatus according to an embodiment of the present invention.

In general, according to one embodiment, a medical image display apparatus includes a thin-out processing unit configured to execute thin-out processing for a series of original medical images, a display unit configured to display the series of medical images generated by the thin-out processing as a moving image and a control unit. The control unit controls the thin-out processing unit to change thin-out ratios on a time axis in the thin-out processing.

An imaging frame rate is the number of frames generated per sec by a medical imaging apparatus such as an X-ray diagnostic apparatus, and is also called an original frame rate. A displaying frame rate is the number of frames switched per sec by a displaying unit including a display, and depends on the execution of the displaying unit. Note that this embodiment uses thin-out processing. Thin-out processing reduces the total number of frames constituting a series of medical images. That is, thin-out processing is the processing of decreasing the frame rate of a series of medical images, and in other words, the processing of increasing the frame period associated with a series of medical images. More specifically, thin-out processing is either the processing of extracting one or a predetermined number of medical images as display target images from a plurality of medical images included in each unit period, typically each 1-sec period, and excluding other medical images from display targets or the processing of generating, as a display target image, an average image of a plurality of medical images included in each unit period.

The thin-out ratio is defined as (N−n)/N. The N is the number of frames of a series of original medical images generated by the medical imaging apparatus in an unit time, typically one second. The N is fixed to 3,000 in this case. The n is the number of frames of images generated by the thin-out processing from the source of the N original images to display on the display unit.

A feature of this embodiment is that it is possible to individually set a thin-out ratio for each unit period for a series of original medical images, as shown in FIGS. 20 and 21. That is, a feature of the embodiment is that thin-out processing is applied to medical images so as to change the thin-out ratio on the time axis. In the cases shown in FIGS. 20 and 21, a series of medical images are generated at an imaging frame rate (3,000 frames/sec) greater than a displaying frame rate (30 frames/sec). Assume that the thin-out ratio is 99%, that is, 2,970 frames are excluded from 3,000 frames in a unit time, typically one second, and 30 frames are extracted as display target images at equal periods, thereby displaying images at a displaying frame rate of 30 frames/sec when n=30 for real-time display. In this case, the motion of the imaging target is reproduced on the same time scale as that at the time of imaging. In contrast, assume that the thin-out ratio is 0%, that is, all the 3,000 frames in a unit time, typically one sec, are displayed as display target images at a displaying frame rate of 30 frames/sec. In this case, the motion of the imaging object is reproduced slowly on a time scale 100 times that at the time of imaging. In the case shown in FIG. 20, the thin-out ratio is set to 0% in the period from time tm to time tm+1, and is set to 99% in other periods. The interpreter sets a thin-out ratio of 0% in a period exhibiting a high degree of importance for diagnosis, and sets a thin-out ratio of 99% in a period exhibiting a low degree of importance for diagnosis, thereby improving the efficiency of interpreting operation. As shown in FIG. 21, it is possible to arbitrarily increase the variations of thin-out ratios.

This embodiment will be described in detail below.

Figure 2:
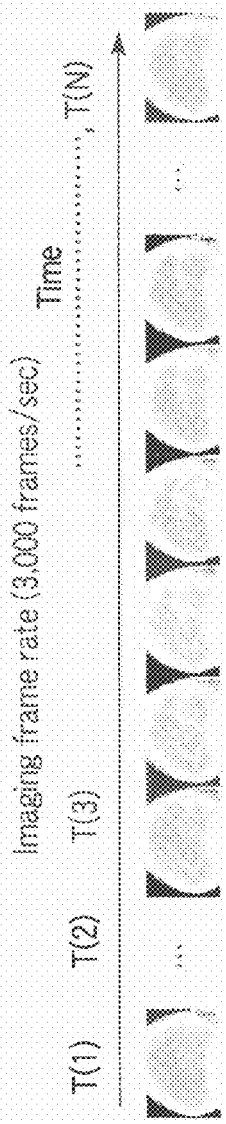
FIG. 2 is a view showing an imaging frame rate in this embodiment.
Figure 3:
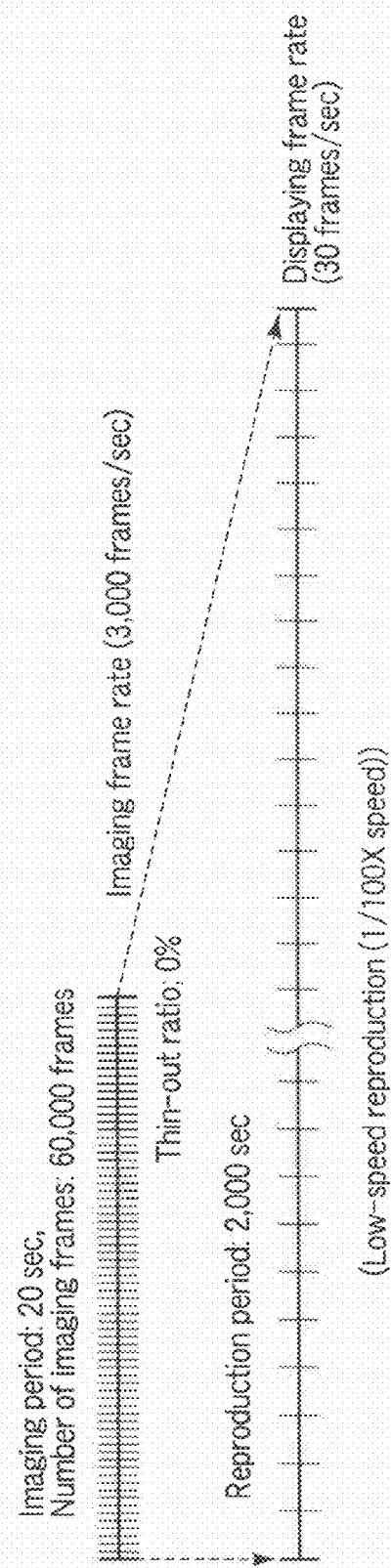
FIG. 3 is a view showing low-speed reproduction (1/100× speed) in this embodiment.

As shown in FIG. 1, the medical image display apparatus according to this embodiment is connected to external imaging generators such as an X-ray diagnostic apparatus 21 and a magnetic resonance diagnostic apparatus (MRI) 22 which are capable of ultrafast imaging and an image archiving communication system (PACS) 23 via an interface unit 11. As shown in FIG. 2, the X-ray diagnostic apparatus 21 and the magnetic resonance diagnostic apparatus 22 each include an ultrafast moving image capturing function of generating a series of medical images constituting a moving image by repeating imaging at a predetermined frame rate of, for example, 3,000 frames/sec. A medical image is typically a two-dimensional image, but may be a three-dimensional image. If a medical image is a three-dimensional image, a "frame" and "frame rate" in the following description are respectively reworded as a "volume" and "volume rate".

Note that a frame rate is defined as the number of frames per unit time, one second in this case. The image generators such as the X-ray diagnostic apparatus 21 and the magnetic resonance diagnostic apparatus 22 transmit a series of medical images generated by their ultrafast moving image capturing functions to the medical image display apparatus according to this embodiment directly or via the image archiving communication system 23. An image storage unit 2 is provided to store the data of the series of original medical images received via the interface unit 11.

In addition to the image storage unit 2 and the interface unit 11, the medical image display apparatus according to this embodiment includes a system control unit 1 as a main control unit, an operation unit 3, an ROI setting unit 4, a TDC generation unit 5, a period-of-interest setting unit 6, a frame rate decision unit 7, a frame rate conversion processing unit 8, a reproduction image storage unit 9, and a display unit 10. The operation unit 3 includes a keyboard and a pointing device such as a mouse. The operator inputs various kinds of instructions to the medical image display apparatus by operating the operation unit 3. For example, the operator selects a specific one medical image (one frame), as an image for designating a region of interest, from a series of medical images via the operation unit 3. The ROI setting unit 4 is provided to express, on the image coordinate system, the position, shape, and size of a region of interest (ROI) designated on a specific medical image via the operation unit 3.

The TDC generation unit 5 generates a temporal change in pixel value (time density curve (TDC)) in the region of interest set by the ROI setting unit 4. When the region of interest includes a plurality of pixels, the TDC generation unit 5 generates a temporal change in arbitrary value such as a median value, pixel value exhibiting the maximum frequency, a maximum value, minimum value, or average pixel value on a pixel value frequency distribution. Note that this temporal change may be a temporal change associated with the distances between a plurality of bone regions, as described later.

The period-of-interest setting unit 6 sets at least one partial period (period of interest) of high interest in an imaging period throughout a series of medical images based on the temporal change generated by the TDC generation unit 5. Note that the period-of-interest setting unit 6 may set the region of interest in accordance with the period designated by the operator via the operation unit 3.

This apparatus reproduces a moving image in a period of interest as part of an imaging period at 1× speed or low speed. The apparatus reproduces a moving image in a period other than the period of interest included in the imaging period at a high speed. 1× speed reproduction is the production of a moving image in a time equivalent to the time required for imaging, that is, the operation of reproducing a moving image, which has been generated in 10 sec, in 10 sec, which is equivalent to the imaging time. The imaging time is the length of time from the start time of imaging to the end time of imaging. The reproduction time is the length of time from the start time of reproduction to the end time of reproduction.

Low-speed reproduction is the production of a moving image in a time longer than that required for imaging, that is, the operation of reproducing a moving image, which has been generated in 10 sec, in, for example, 20 sec, which is longer than the imaging time. High-speed reproduction is the production of a moving image in a time shorter than that required for imaging, that is, the operation of reproducing a moving image, which has been generated in 10 sec, in, for example, 5 sec, which is shorter than the imaging time.

Note that a reproduction speed is defined as a ratio n of an imaging time to a reproduction time (n=imaging time/reproduction time). In general, a reproduction speed is expressed by "n× speed". In this embodiment, a plurality of reproduction speeds are prepared for each of low-speed reproduction and high-speed reproduction. A reproduction speed is determined by the thin-out ratio set by the frame rate conversion processing unit 8 and the displaying frame rate of the display unit 10. The frame rate conversion processing unit 8 executes a thin-out processing for a series of generated original medical images to thin-out or smooth the original medical images. Note that the displaying frame rate of the display unit 10 may be fixed to, for example, 30 frames/sec or may be selected from two kinds of displaying frame rates, e.g., 30 frames/sec and 60 frames/sec. This embodiment will exemplify the former case.

This embodiment uses a very high imaging frame rate, e.g., 3,000 frames/sec, for ultrafast imaging. The displaying frame rate of the display unit 10 is 30 frames/sec or 60 frames/sec, which is much smaller than the imaging frame rate. When a displaying frame rate is fixed, the final reproduction speed of a moving image displayed by the display unit 10 is decided by an imaging frame rate and a thin-out ratio.

The frame rate decision unit 7 individually assigns thin-out ratios to at least one period of interest of partial periods of an imaging time and a period (period of low interest) of other partial periods of the imaging time. As described above, a frame rate is defined as the number of frames per unit time. The thin-out ratio assigned to a period of interest is smaller than thin-out ratios assigned to each of other periods of low interest. In other words, the reproduction speed in a period of interest is slower than in a period of low interest, and the reproduction speed in a period of low interest is set to be faster than that in a period of interest. The frame rate decision unit 7 assigns different thin-out ratios to a period of interest and a period of low interest so as to make moving image reproduction fall within the reproduction time frame designated by the operator, typically the interpreter, via the operation unit 3. This operation will be described in detail later.

The frame rate conversion processing unit 8 executes a thin-out processing for a series of generated original medical images to thin-out or smooth the original medical images in the thin-out ratio decided by the frame rate decision unit 7. Thin-out processing is the processing of decreasing the frame rate of a series of medical images. More specifically, thin-out processing is either the processing of extracting one or a predetermined number of medical images as display target images from a plurality of medical images included in each unit period, typically each 1-sec period, and excluding other medical images from display targets or the processing of generating, as a display target image, an average image of a plurality of medical images included in each unit period. The former case will be described below. A thin-out ratio is obtained as (N−n)/N where N is the number of frames included in a unit period (one sec) and n is the number of frames of display target images in the period.

The reproduction image storage unit 9 is provided to store the data of a series of medical images as reproduction targets which are converted by the frame rate conversion processing unit 8. The number of frames of a series of medical images as reproduction targets is smaller than that of a series of original medical images. In addition, the number of frames of medical images in a period of interest is larger than that of medical images in a period of low interest.

The data of a series of medical images as reproduction targets stored in the reproduction image storage unit 9 are sequentially supplied to the display unit 10 frame by frame at a predetermined period in synchronism with vertical sync signals for the display unit 10 under the control of the system control unit 1.

FIGS. 3, 4, 5, 6, and 7 show a plurality of reproduction speeds when the displaying frame rate is fixed to 30 frames/sec. In reproduction at the lowest speed shown in FIG. 3, all the generated frames are display targets. The thin-out ratio is 0. In this case, the reproduction speed is 1/100× speed, and hence the motion of an organ or the like is reproduced very slowly apparently on the display. In low-speed reproduction shown in FIG. 4, the thin-out ratio is set to 90%. In this case, the reproduction speed is 1/10× speed, and hence the motion of an organ or the like is reproduced slowly apparently on the display.

Figure 5:
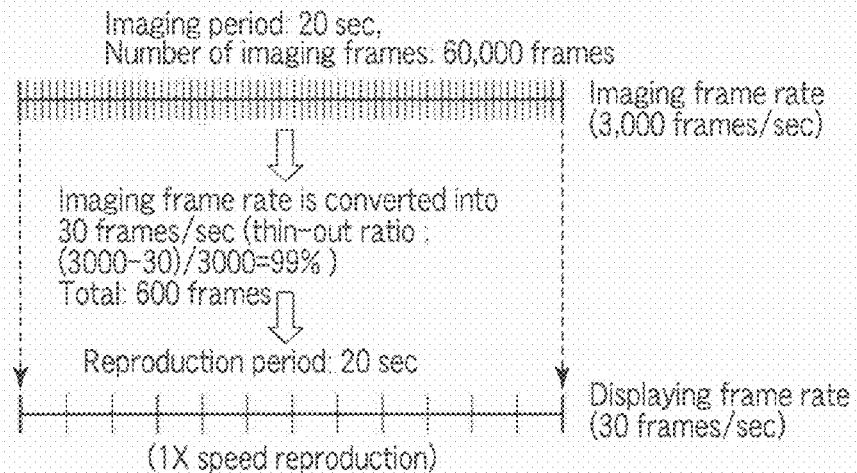
FIG. 5 is a view showing 1× speed reproduction in this embodiment.

In 1× speed reproduction shown in FIG. 5, the thin-out ratio is set to 99%. In this case, the reproduction speed is 1× speed, and hence the motion of an organ or the like is reproduced at the same speed as that of actual motion apparently on the display.

Figure 6:
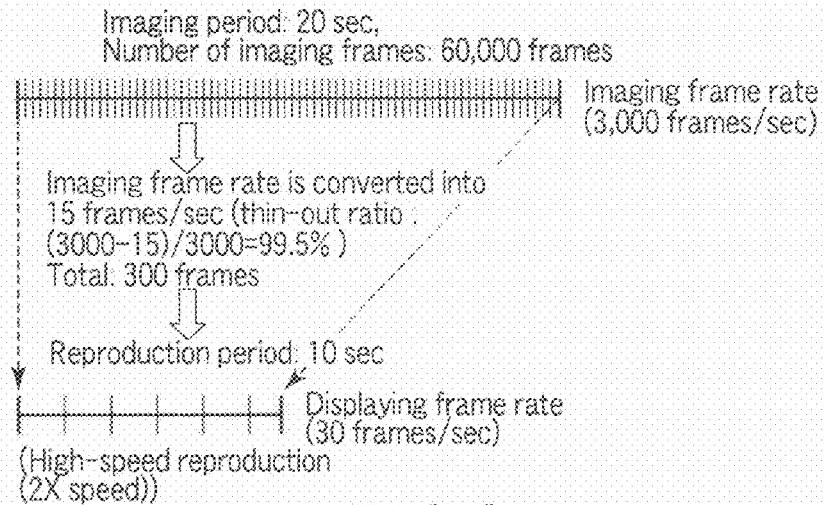
FIG. 6 is a view showing high-speed reproduction (2× speed) in this embodiment.
Figure 7:
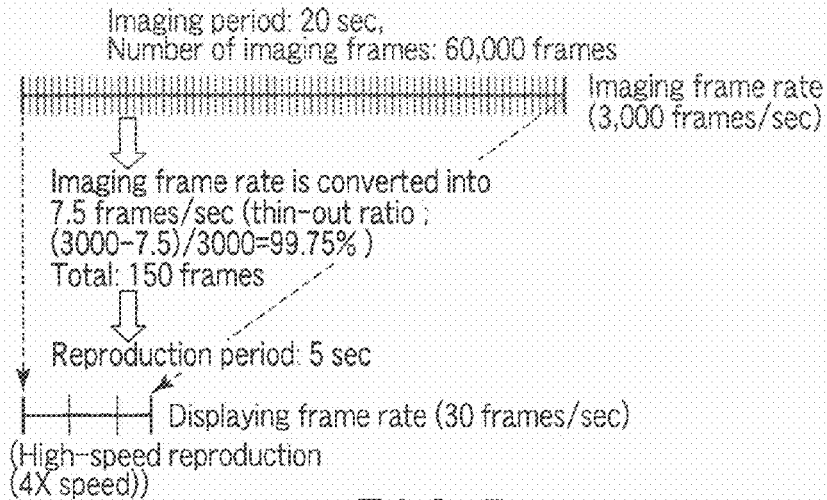
FIG. 7 is a view showing high-speed reproduction (4× speed) in this embodiment.
Figure 8:
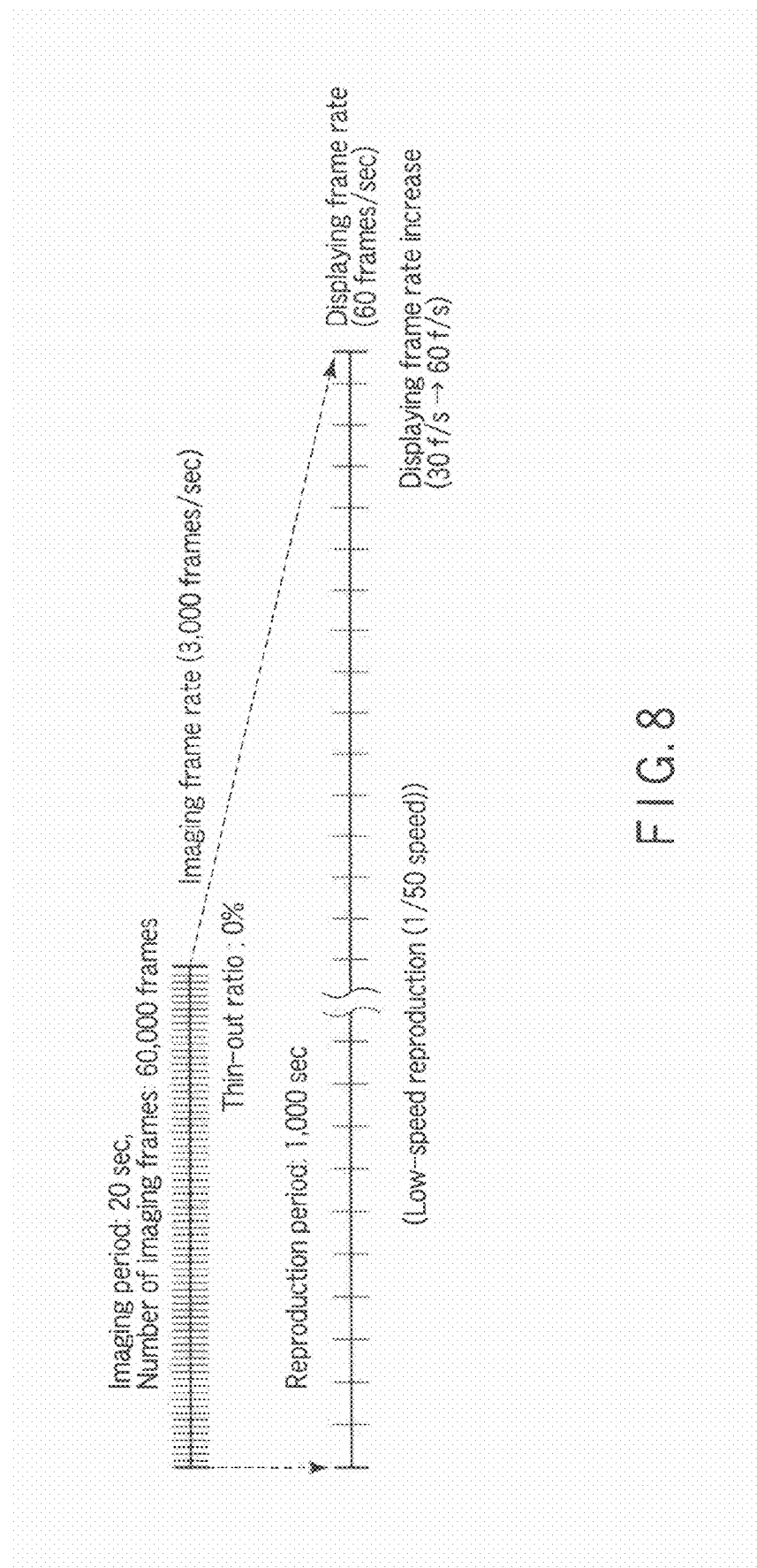
FIG. 8 is a view showing low-speed reproduction (1/50× speed) in this embodiment.

In high-speed reproduction shown in FIG. 6, the thin-out ratio is set to 99.5%. In this case, the reproduction speed is 2× speed, and hence the motion of an organ or the like is reproduced at 2× speed apparently on the display. In high-speed reproduction shown in FIG. 7, the thin-out ratio is set to 99.75%. In this case, the reproduction speed is 4× speed, and hence the motion of an organ or the like is reproduced at 4× speed apparently on the display.

FIGS. 8, 9, 10, and 11 show displaying frame rates corresponding to a plurality of reproduction speeds when the displaying frame rate is changed (increased) from 30 frames/sec to 60 frames/sec. In the case shown in FIG. 8, no thin-out processing is executed, and the thin-out ratio is 0%. In this case, the reproduction speed is 1/50× speed, and hence the motion of an organ or the like is reproduced very slowly apparently, at the next lowest speed relative to the case shown in FIG. 3.

Figure 9:
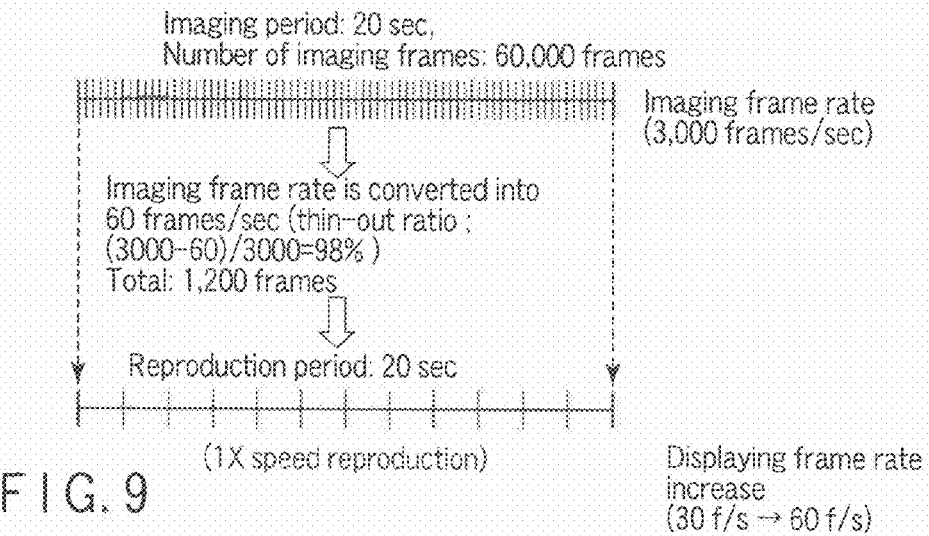
FIG. 9 is a view showing 1× speed reproduction accompanied by an increase in displaying frame rate in this embodiment.

As the displaying frame rate shown in FIG. 9 is changed to a very high frame rate of 60 frames/sec, 1× speed reproduction is implemented as in the case shown in FIG. 5. The thin-out ratio is set to 98%.

Figure 10:
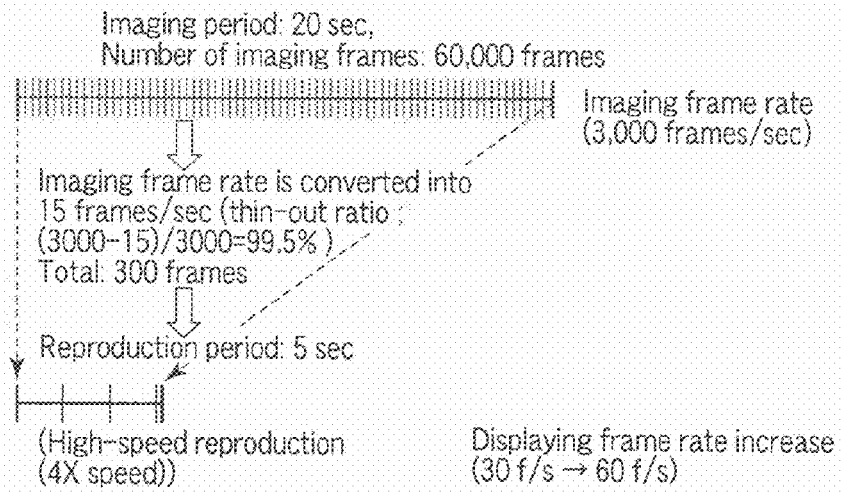
FIG. 10 is a view showing high-speed reproduction (4× speed) accompanied by an increase in displaying frame rate in this embodiment.

In the case shown in FIG. 10, the displaying frame rate is changed from 30 frames/sec to 60 frames/sec. In this case, 4× speed reproduction is implemented as in the case shown in FIG. 7. The thin-out ratio is 99.5%.

Figure 11:
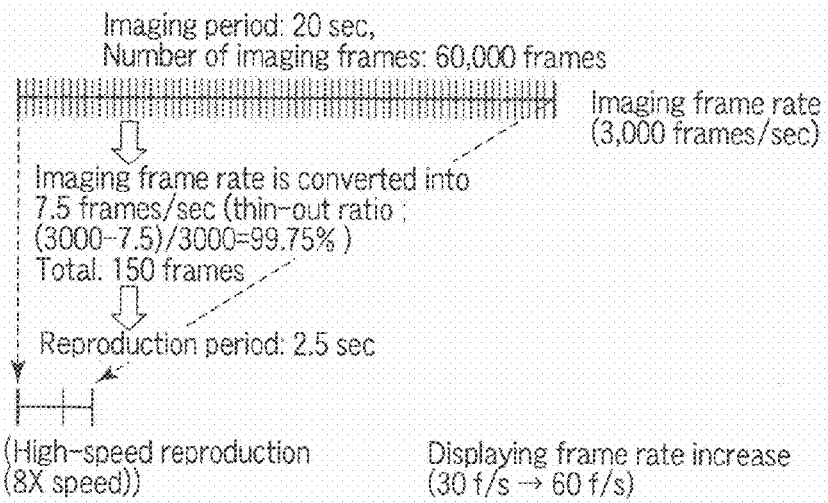
FIG. 11 is a view showing high-speed reproduction (8× speed) accompanied by an increase in displaying frame rate in this embodiment.

In the displaying frame rate in highest-speed reproduction shown in FIG. 11, 8× speed reproduction is implemented. The thin-out ratio is set to 99.75%.

When the displaying frame rate of the display unit 10 is fixed to 30 frames/sec, the system control unit 1 instructs the frame rate decision unit 7 to limit the choices of thin-out ratios to five types of thin-out ratios shown in FIGS. 3, 4, 5, 6, and 7.

Assume that it is possible to select 30 frames/sec or 60 frames/sec as the displaying frame rate of the display unit 10, and the interpreter has designated an increase in displaying frame rate to 60 frames/sec via the display unit 10. In this case, the system control unit 1 instructs the frame rate decision unit 7 to limit the choices of thin-out ratios to four types of thin-out ratios shown in FIGS. 8, 9, 10, and 11.

Assume also that it is possible to select 30 frames/sec or 60 frames/sec as the displaying frame rate of the display unit 10, and the interpreter has permitted to increase the displaying frame rate to 60 frames/sec via the operation unit 3. In this case, the system control unit 1 selects either 30 frames/sec or 60 frames/sec as a displaying frame rate. The displaying frame rate is fixed throughout the entire reproduction period. If, for example, the ratio of the reproduction time frame designated by the interpreter to the imaging time is twice or more, the system control unit 1 selects 30 frames/sec as a displaying frame rate. If the ratio of the reproduction time frame designated by the interpreter to the imaging time is less than twice, the system control unit 1 selects 60 frames/sec as a displaying frame rate, and adds 8× speed reproduction to the choices of displaying frame rates.

Figure 12:
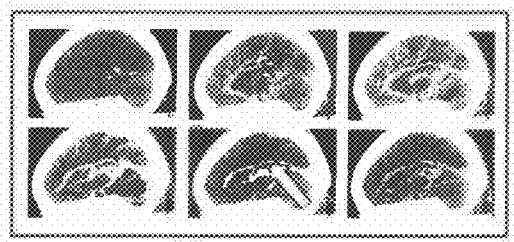
FIG. 12 is a view showing an image selection window for setting a region of interest (ROI) in this embodiment.
Figure 13:
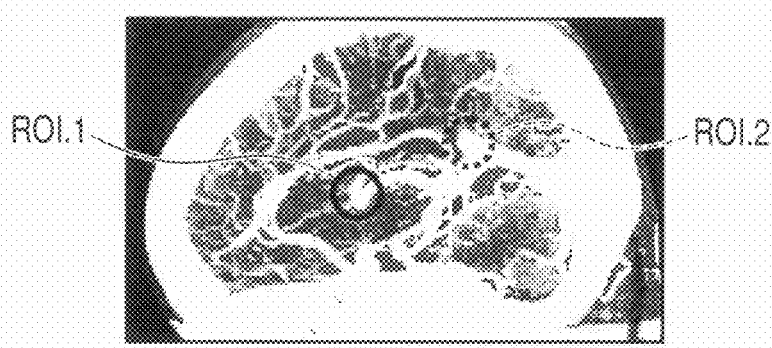
FIG. 13 is a view showing a region of interest set on the image selected in FIG. 12.

An example of how a period of interest is set will be described next. First of all, a predetermined number of medical images are selected discretely on the time axis from the series of medical images generated by imaging, under the control of the system control unit 1. A frame rate conversion processing unit (not shown) reduces the predetermined number of selected medical images to a matrix size. With this processing, the predetermined number of thumbnail medical images are generated, which are then displayed as a list on the display unit 10, as shown in FIG. 12. The interpreter then selects a specific medical image by operating the operation unit 3. As shown in FIG. 13, the selected medical image is displayed in the entire display frame of the display unit 10 in the original matrix size or in a matrix size larger than that of the thumbnails. The interpreter operates the operation unit 3 to designate one or a plurality of regions of interest (ROIs) at arbitrarily positions on the displayed medical image in an arbitrary shape and size. The following description is based on the assumption that the interpreter designates two regions of interest. The ROI setting unit 4 sets the position, shape, and size of each region of interest (ROI), designated on the specific medical image via the operation unit 3, in an expression on the image coordinate system.

The TDC generation unit 5 generates temporal changes (TDCs) in pixel value in the regions of interest set by the ROI setting unit 4 with respect to all the series of medical images constituting the generated moving image. If a region of interest includes a plurality of pixels, a temporal change (TDC) in average pixel value is typically generated. The display unit 10 displays the generated TDCs.

Figure 14:
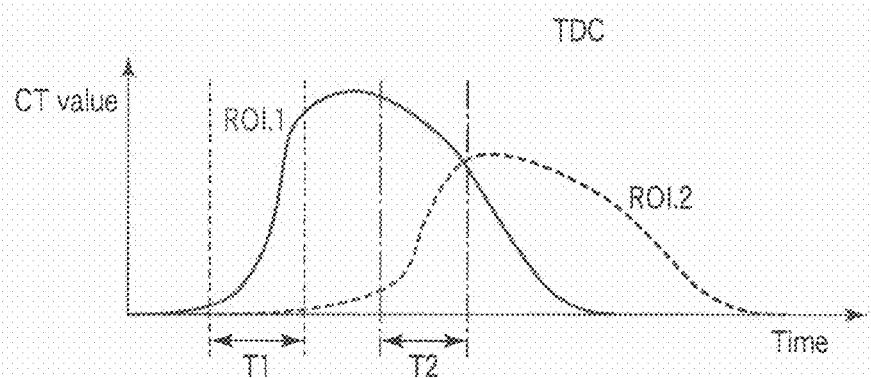
FIG. 14 is a graph showing temporal changes in pixel value (contrast density) associated with the region of interest in FIG. 13 and periods of interest specified based on the temporal changes.

FIG. 14 shows two TDCs associated with two regions of interest ROI. 1 and ROI. 2. In the case shown in FIG. 14, the TDCs are based on contrast-enhanced imaging. When, for example, the interpreter sets, as periods of interest, periods in which a contrast medium rapidly flows into regions of interest, the period-of-interest setting unit 6 sets periods in which the differential values of TDCs are equal to or more than a predetermined threshold, as periods of interest T1 and T2. Note that the operator may set at least one region of period on a TDC displayed on the display unit 10 via the operation unit 3. The operator may correct the periods of interests T1 and T2, set by the period-of-interest setting unit 6, via the operation unit 3.

The frame rate decision unit 7 assigns, to the set periods of interest T1 and T2, displaying frame rates for the periods of interest which are initially set by the interpreter, and also assigns, to periods of low interest other than the periods of interest T1 and T2, thin-out ratios for regions of low interest which are initially set by the interpreter. For example, the frame rate decision unit 7 assigns low-speed reproduction at 1/10× speed shown in FIG. 4 to the periods of interests T1 and T2, and high-speed reproduction at 2× speed shown in FIG. 6 to periods of low interest. When the total reproduction time calculated based on these initial thin-out ratios falls within a pre-designated reproduction time frame, the initial thin-out ratios are confirmed. If the calculated total reproduction time exceeds the pre-designated reproduction time frame, these initial thin-out ratios are changed according to a predetermined rule. First of all, the thin-out ratio for the periods of low interest is lowered by one step. In this case, the thin-out ratio for implementing high-speed reproduction at 2× speed shown in FIG. 6 is changed to the thin-out ratio for implementing high-speed reproduction at 4× speed shown in FIG. 7. If the total reproduction time re-calculated based on the changed thin-out ratio falls within the pre-designated reproduction time frame, the thin-out ratio is confirmed. If the re-calculated total reproduction time exceeds the pre-designated reproduction time frame, the thin-out ratio for the regions of interest T1 and T2 is lowered by one step. In this case, the thin-out ratio for implementing low-speed reproduction at 1/10× speed shown in FIG. 4 is changed to the thin-out ratio for implementing the 1× speed reproduction shown in FIG. 5. If the total reproduction time re-calculated based on the changed thin-out ratio falls within the pre-designated reproduction time frame, the displaying frame rate is confirmed. When the total reproduction time finally exceeds the reproduction time frame, a warning message indicating the excess is displayed. When the interpreter inputs "OK" instruction, the thin-out ratio is confirmed. When the interpreter inputs "NG" instruction, the system control unit 1 displays TDCs and prompts the interpreter to shorten the periods of interest T1 and T2 or execute the designating operation of excluding partial periods from reproduction.

For the sake of descriptive convenience, assume that a thin-out ratio for implementing low-speed reproduction at 1/10× speed shown in FIG. 4 is confirmed for the periods of interest T1 and T2, and a thin-out ratio for implementing high-speed reproduction at 2× speed shown in FIG. 6 is confirmed for periods of low interest.

When thin-out ratios are confirmed for the periods of interest T1 and T2 and the periods of low interest, the frame rate conversion processing unit 8 executes thin-out processing for the series of original medical images in accordance with the confirmed thin-out ratios. The frame rate conversion processing unit 8 extracts reproduction target images from a plurality of medical images generated in the periods of interest T1 and T2 at equal periods along the time axis, at a rate of one frame per 10 frames in this case, in accordance with the thin-out ratio corresponding to the thin-out ratio confirmed for the periods of interest T1 and T2, and excludes other medical images from reproduction targets, i.e., thins out them. Likewise, the frame rate conversion processing unit 8 extracts reproduction target images from a plurality of medical images generated in the regions of low interest at equal periods along the time axis, at a rate of one frame per 200 frames in this case, and excludes other medical images from reproduction targets, i.e., thins out them.

Figure 15:
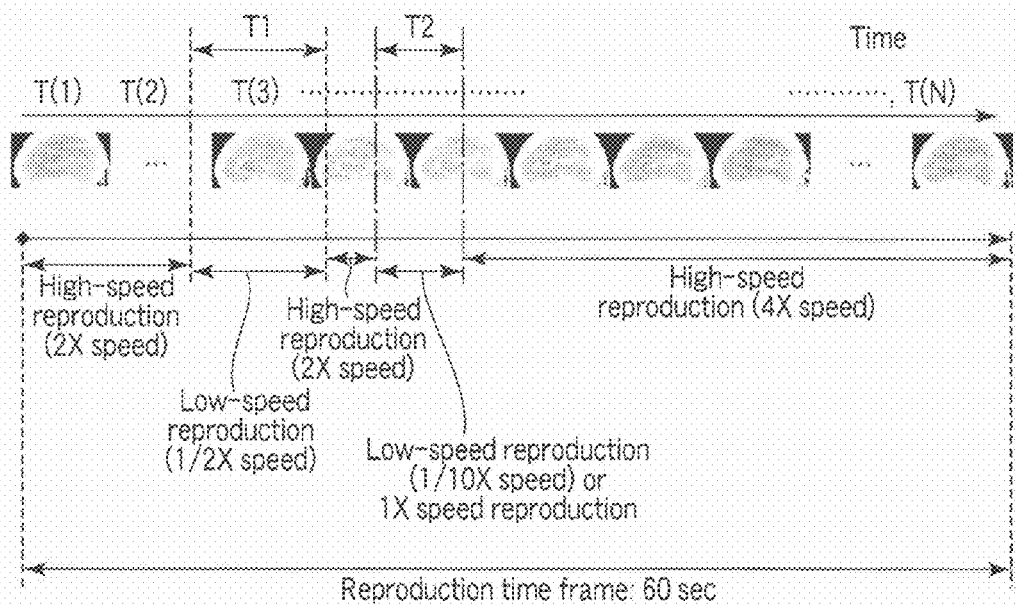
FIG. 15 is a view showing reproduction speeds in the periods of interest in FIG. 14 and other periods.

The reproduction image storage unit 9 temporarily stores the series of reproduction target images extracted by the frame rate conversion processing unit 8, and sequentially supplies them frame by frame to the display unit 10 at a predetermined period in synchronism with vertical sync signals for the display unit 10 under the control of the system control unit 1. With this operation, the display unit 10 reproduces images at a low speed in the regions of interest and at a high speed in the regions of low interest, as shown in FIG. 15. In this manner, a series of medical images as reproduction targets are reproduced at various speeds along the reproduction time axis in accordance with the degrees of interest.

In this case, when dynamically observing a blood vessel or the like with a contrast medium, the operator sets an ROI on an aneurysma, AVM, or the like to be observed. The operator can observe the flow of a contrast medium by high-speed reproduction until the contrast medium reaches the ROI, and observe the dynamics of a flood flow in detail in a period from the instant the contrast medium flows into the ROI to the instant immediately before the inflow of the contrast medium reaches a peak. Thereafter, the operator observes the flow of the contrast medium in high-speed reproduction. In this manner, it is possible to slowly interpret a series of medical images generated by ultrafast imaging when observing dynamics of relatively high interest while reproducing medical images at a high speed when observing dynamics of relatively low interest without excluding them from reproduction targets. This makes it possible to improve the interpretation efficiency while suppressing a deterioration in interpretation accuracy.

Figure 16:
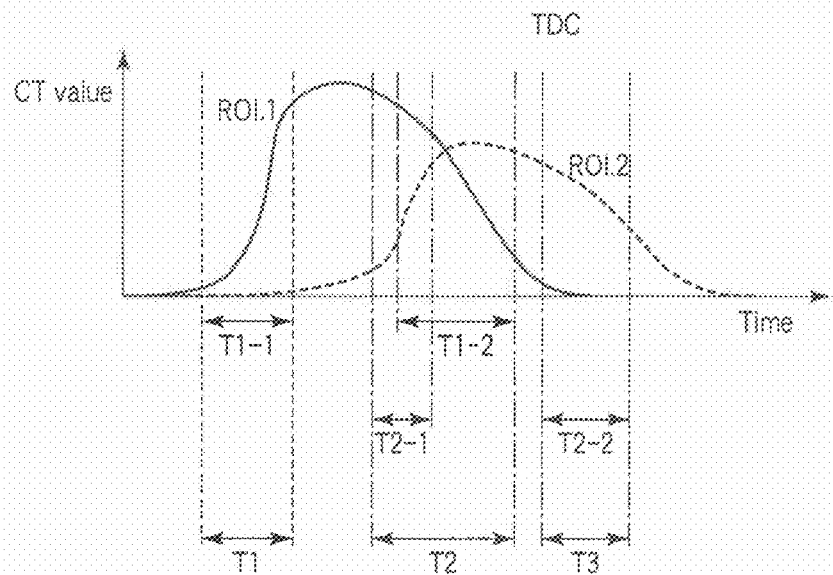
FIG. 16 is a graph showing temporal changes in pixel value (contrast density) associated with the regions of interest in FIG. 13 and periods of interest specified based on the temporal changes.
Figure 17:
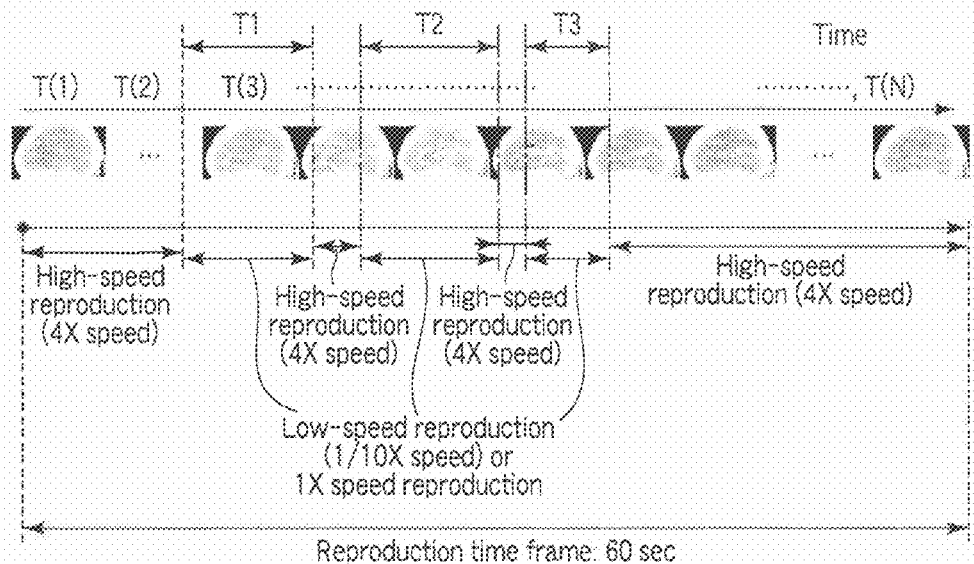
FIG. 17 is a view showing reproduction speeds in the periods of interest in FIG. 16 and other periods.

Note that periods of interest may be set in a contrast medium outflow period as well as a contrast medium inflow period. In this case, as shown in FIG. 16, a plurality of periods of interest may overlap each other. In the case shown in FIG. 16, a period of interest T2-1 of a contrast medium outflow associated with the second ROI overlaps a period of interest T1-2 of a contrast medium inflow associated with the first ROI. In this case, a period of interest T2 is set in a period including both the period of interest T2-1 and the period of interest T1-2. Image data are reproduced slowly in the three set periods of interest T1, T2, and T3 as shown in FIG. 17, and are reproduced at a high speed in periods of low interest.

In this case, when dynamically observing a blood vessel or the like with a contrast medium, it is possible to set an ROI on an aneurysm, AVM, or the like to be observed, observe the flow of the contrast medium by executing high-speed reproduction until the arrival of the contrast medium at the ROI, and observe the dynamics of the contrast medium in detail by executing low-speed reproduction in a period in which the contrast medium inflows. It is also possible to shorten the reproduction time by executing high-speed reproduction when the contrast medium density exhibits no change, observe the state of outflow of the contrast medium in detail in a period in which the contrast medium outflows, and shorten the reproduction time by executing high-speed reproduction in a period after the contrast medium sufficiently outflows from the region of interest. That is, the interpretation accuracy is improved by executing low-speed reproduction in an important period, and the interpretation efficiency is improved by executing high-speed reproduction in a less important period. Since a moving image portion in a period which is considered not so important is not excluded from reproduction targets, it is possible to reduce the chance to overlook any important dynamics in the period.

As methods of setting periods of interest, various other methods may be used. In joint examination, some patients may feel pain, although no abnormality is detected by normal imaging. In such a case, for example in the embodiment of FIG. 18, the doctor may want to observe the motion of a joint (to make a treatment plan by checking contact between the bones or joint displacement at a given place) while imaging the moving joint. The gap between the bones is checked, and the joint is displayed slowly only in a period in which no gap is detected. In the case of a joint, the doctor wants to mainly observe a place where the gap is smallest, and hence it is necessary to slowly display such a place in a period from the instant the differential value of temporal changes in gap exhibits a negative maximum value to the instant the differential value exhibits a positive maximum value.

For example, as shown in FIGS. 18 and 19, when observing a joint, importance is placed on the distance between the two bone regions of the joint portion. The distance between the two bone regions set on a specific medical image is calculated, and a temporal change is generated. A period in which the distance between the two bone regions is smaller than a predetermined distance is set as a period of interest. That is, the motions of the bones which interfere with each other or approach are slowly reproduced, while high-speed reproduction is executed in other periods in which the bones are spaced apart from each other to some extent.

As described above, when reproducing a series of medical images generated by ultrafast imaging, the reproduction speed is changed by changing the thin-out ratio along the time axis in accordance with whether a given period is important. In other words, changing the thin-out ratio or smoothing ratio along the time axis can implement efficient observation of a large amount of medical image data while improving the diagnosis efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus comprising:
   an image storing unit configured to store a series of original medical images;
   a temporal change generation unit configured to generate a pixel value temporal change associated with a region of interest based on the series of original medical images;
   a thin-out processing unit configured to execute thin-out processing for a series of original medical images based on the pixel value temporal change, when reproducing the series of original medical images;
   a controller configured to control the thin-out processing unit to assign different thin-out ratios in a first period of an imaging time and in a second different period of the imaging time, during continuous display of the series of original medical images; and
   a display unit configured to display the series of medical images generated by the thin-out processing as a moving image;
   wherein the thin-out processing comprises averaging a plurality of images from the series of medical images based on the assigned thin out ratios to generate a series of averaged images, and the display unit is configured to display the series of averaged images in the respective first and second periods, and
   wherein a displaying frame rate of the display unit is smaller than a frame rate of the series of original medical images.

2. The apparatus of claim 1, wherein the total number of frames constituting the series of original medical images is reduced by the thin-out processing.

3. The apparatus of claim 1, further comprising a thin-out ratio decision unit configured to decide a combination of the thin-out ratios such that a reproduced display of the series of medical images falls within a time frame designated by an operator.

4. The apparatus of claim 3, wherein the thin-out ratio decision unit decides a combination of the thin-out ratios such that the thin-out ratio in an period of interest designated by an operator becomes smaller than the thin-out ratio in an period other than the period of interest.

5. The apparatus of claim 1, further comprising:
   a region-of-interest specifying unit configured to specify at least one period of interest based on the generated temporal change; and
   a thin-out ratio decision unit configured to decide the thin-out ratio such that the thin-out ratio in the period of interest becomes smaller than the thin-out ratio in an period other than the period of interest.

6. The apparatus of claim 5, further comprising an operation unit configured to allow an operator to designate the plurality of regions of interest on the medical image.

7. The apparatus of claim 5, wherein
   the period-of-interest setting unit sets period in which the differential values of the generated temporal change are equal to or more than a predetermined threshold, as periods of interest.

8. The apparatus of claim 5, wherein
when the region of interest includes a plurality of pixels, the temporal change generation unit generates the pixel value temporal change in accordance with at least one of a median value, a pixel value exhibiting a maximum frequency, a maximum value, a minimum value, and an average value on a pixel value frequency distribution in the region of interest.

9. The apparatus of claim 5, wherein
the pixel value temporal change is associated with a distance between a plurality of predetermined regions.

10. The apparatus of claim 9, wherein
the plurality of predetermined regions is a plurality of bone regions.

11. The apparatus of claim 10, wherein
the region-of-interest specifying unit is configured to set a period in which the distance between the plurality of bone regions is smaller than a predetermined distance as the period of interest.

12. The apparatus of claim 1, wherein the control unit controls the display unit so as to change a displaying frame rate of the display unit on the time axis, together with the thin-out ratio.

13. The apparatus of claim 1, wherein the thin-out processing sets the thin-out ratio for each unit period.

14. The apparatus of claim 1, wherein
thin-out ratios in the first and second periods are greater than zero.

15. The apparatus of claim 1, wherein
the displaying frame rate is fixed throughout the entire reproduction period.

16. An X-ray computed tomography apparatus comprising:
a gantry unit configured to acquire projection data associated with an object;
a reconstruction unit configured to reconstruct data of a series of medical images based on the projection data;
an image storing unit configured to store a series of original medical images;
a temporal change generation unit configured to generate a pixel value temporal change associated with a region of interest based on the series of original medical images;
a thin-out processing unit configured to execute thin-out processing for a series of medical images based on the pixel value temporal change, when reproducing the series of original medical images;
a controller configured to control the thin-out processing unit to assign different thin-out ratios in a first period of an imaging time and in a second different period of the imaging time, during continuous display of the series of original medical images; and
a display unit configured to display the series of medical images having undergone the thin-out processing as a moving image;
wherein the thin-out processing comprises averaging a plurality of images from the series of medical images based on the assigned thin out ratios to generate a series of averaged images, and the display unit is configured to display the series of averaged images in the respective first and second periods, and
wherein the series of original medical images are generated in a frame rate greater than a displaying frame rate of the display unit.

17. The apparatus of claim 16, wherein the total number of frames constituting the series of medical images is reduced by the thin-out processing.

18. The apparatus of claim 16, further comprising a thin-out ratio decision unit configured to decide a combination of the thin-out ratios such that a reproduced display of the series of medical images falls within a time frame designated by an operator.

19. The apparatus of claim 18, wherein the thin-out ratio decision unit decides a combination of the thin-out ratios such that the thin-out ratio in a period of interest designated by an operator becomes smaller than the thin-out ratio in an period other than the period of interest.

20. The apparatus of claim 16, further comprising:
a region-of-interest specifying unit configured to specify at least one period of interest based on the generated temporal change; and
a thin-out ratio decision unit configured to decide the thin-out ratio such that the thin-out ratio in the period of interest becomes smaller than the thin-out ratio in an period other than the period of interest.

21. The apparatus of claim 20, further comprising an operation unit configured to allow an operator to designate the plurality of regions of interest on the medical image.

22. The apparatus of claim 20, wherein
the period-of-interest setting unit sets period in which the differential values of the generated temporal change are equal to or more than a predetermined threshold, as periods of interest.

23. The apparatus of claim 20, wherein
when the region of interest includes a plurality of pixels, the temporal change generation unit generates the pixel value temporal change in accordance with at least one of a median value, a pixel value exhibiting a maximum frequency, a maximum value, a minimum value, and an average value on a pixel value frequency distribution in the region of interest.

24. The apparatus of claim 20, wherein
the pixel value temporal change is associated with a distance between a plurality of predetermined regions.

25. The apparatus of claim 24, wherein
the plurality of predetermined regions is a plurality of bone regions.

26. The apparatus of claim 25, wherein
the region-of-interest specifying unit configured to set a period in which the distance between the plurality of bone regions is smaller than a predetermined distance as the period of interest.

27. The apparatus of claim 16, wherein the control unit controls the display unit so as to change a displaying frame rate of the display unit on the time axis, together with the thin-out ratio.

28. The apparatus of claim 16, wherein the thin-out processing sets the thin-out ratio for each unit period.

29. The apparatus of claim 16, wherein
thin-out ratios in the first and second periods are greater than zero.

30. The apparatus of claim 16, wherein
the displaying frame rate is fixed throughout the entire reproduction period.

* * * * *